United States Patent
Lammerant

(10) Patent No.: US 10,416,074 B2
(45) Date of Patent: Sep. 17, 2019

(54) SPECTROMETER CALIBRATION METHOD AND REFERENCE MATERIAL

(71) Applicant: Heraeus Electro-Nite International N.V., Houthalen (BE)

(72) Inventor: Luc Lammerant, Koersel (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 9 days.

(21) Appl. No.: 15/097,418

(22) Filed: Apr. 13, 2016

(65) Prior Publication Data

US 2016/0305867 A1 Oct. 20, 2016

(30) Foreign Application Priority Data

Apr. 16, 2015 (EP) .................................. 15163879

(51) Int. Cl.
*G01N 21/27* (2006.01)
*G01J 3/28* (2006.01)

(52) U.S. Cl.
CPC ......... *G01N 21/278* (2013.01); *G01N 21/274* (2013.01); *G01J 3/28* (2013.01); *G01J 2003/2866* (2013.01); *G01N 21/276* (2013.01); *G01N 2201/13* (2013.01)

(58) Field of Classification Search
CPC ............... G01N 21/274; G01N 21/278; G01N 2201/13; G01N 21/276; G01J 3/28; G01J 2003/2866
See application file for complete search history.

(56) References Cited

U.S. PATENT DOCUMENTS

| | | | |
|---|---|---|---|
| 3,791,220 A | 2/1974 | Falk et al. | |
| 4,189,204 A | 2/1980 | Brown et al. | |
| 4,566,343 A | 1/1986 | Theuwis et al. | |
| 5,139,332 A * | 8/1992 | Kitaoka | G01N 21/62 356/243.2 |
| 5,774,326 A | 6/1998 | McConnelee et al. | |
| 7,468,088 B1 * | 12/2008 | Blankenhorn | C22B 21/06 75/10.18 |
| 7,480,042 B1 | 1/2009 | Phillips et al. | |
| 2003/0236642 A1* | 12/2003 | Timans | G01J 5/0003 702/99 |
| 2004/0206730 A1* | 10/2004 | Holber | H01J 37/32009 219/121.52 |
| 2004/0262510 A1 | 12/2004 | Springsteen et al. | |

(Continued)

FOREIGN PATENT DOCUMENTS

| | | |
|---|---|---|
| CN | 201429713 Y | 3/2010 |
| DE | 10202357 A1 | 1/2003 |

(Continued)

OTHER PUBLICATIONS

Extended Search Report dated Oct. 28, 2015 in EP Application No. 15163879.8.

(Continued)

*Primary Examiner* — Sang H Nguyen
(74) *Attorney, Agent, or Firm* — Panitch Schwarze Belisario & Nadel LLP

(57) ABSTRACT

A calibration method for a spectrometer and a reference material which facilitates calibration of the spectrometer are provided. The reference material has a homogeneous content of elements protected by an inert coating.

17 Claims, 5 Drawing Sheets

(56) References Cited

U.S. PATENT DOCUMENTS

| | | | |
|---|---|---|---|
| 2008/0085212 A1* | 4/2008 | Adams | G01N 29/036 422/50 |
| 2009/0075236 A1 | 3/2009 | Towse et al. | |
| 2011/0159314 A1* | 6/2011 | Kim | C22C 38/02 428/653 |
| 2011/0293547 A1* | 12/2011 | Geissler | C09C 1/0015 424/63 |
| 2012/0231374 A1* | 9/2012 | Iseki | H01M 8/0234 429/518 |
| 2013/0049575 A1* | 2/2013 | Fujita | C03C 8/08 313/503 |
| 2013/0050694 A1* | 2/2013 | Janssen | G01N 21/648 356/301 |
| 2013/0209790 A1* | 8/2013 | Geissler | B82Y 30/00 428/329 |
| 2014/0204377 A1* | 7/2014 | Day | G01J 3/443 356/318 |
| 2015/0143806 A1* | 5/2015 | Friesth | F24S 25/50 60/517 |
| 2016/0084802 A1* | 3/2016 | Yusuf | G01N 29/12 73/582 |
| 2016/0258815 A1* | 9/2016 | Barefield, II | F16B 2/08 |
| 2016/0280811 A1* | 9/2016 | Proust | C08F 8/32 |
| 2016/0298783 A1* | 10/2016 | Chun | F16K 31/002 |

FOREIGN PATENT DOCUMENTS

| | | | |
|---|---|---|---|
| EP | 0237056 A2 | | 9/1987 |
| EP | 1059657 A2 * | | 12/2000 ... H01J 49/0009 |
| EP | 1227312 A1 | | 7/2002 |
| GB | 1411722 A | | 10/1975 |
| GB | 1470811 A | | 4/1977 |
| JP | H07151607 A | | 6/1995 |
| JP | H07-229791 A | | 8/1995 |
| JP | H0875553 A | | 3/1996 |
| JP | 2010-071666 A | | 4/2010 |
| JP | 2011169917 A | | 9/2011 |

OTHER PUBLICATIONS

Skarp et al., "Problem Solving in the Upgrading of Product Offerings—A Case Study from the Steel Industry", Industrial Marketing Manager, Elsevier, vol. 37, No. 6, pp. 725-737 (Aug. 2008).

Wilken et al., "Electrical Measurements at Radio Frequency Glow Discharges for Spectroscopy", Spectrochimica Acta, vol. 62. No. 10, pp. 1085-1122 (Sep. 2007) 1885-1122.

Pretrial Re-Examination Report dated Mar. 29, 2019 in JP Application No. 2014-088614.

Extended Search Report dated Dec. 21, 2015 in EP Application No. 15171672.7.

Dulski, "A Manual for the Chemical Analysis of Metals," ASTM International (1996).

MBH Catalogue 2014 from MBH Analytical LTD, Holland House, Queens Road, Barnet, EN5 4DJ, England.

ASTM, "Standard Test Method for Analysis of Carbon and Low-Alloy Steel by Spark Atomic Emission Spectrometry," Mar. 1, 2016, pp. 1-11, Retrieved from the Internet: URL:http://www.astm.org/cgi-bin/resolver.cgi?E415-15, {Retrieved on Oct. 11, 2018}.

Office Action dated Oct. 17, 2018 in EP Application No. 15163879.8.

* cited by examiner

SPECTROMETER CALIBRATION METHOD AND REFERENCE MATERIAL

BACKGROUND OF THE INVENTION

The present invention refers to a calibration method for a spectrometer and a reference material used for calibration.

The composition of iron and steel alloys can be measured using different analytical techniques. One of these techniques, optical emission spectroscopy, involves exciting atoms of a target sample of which knowledge of the composition is desired and examining the wavelength of photons emitted by atoms during transition from an excited state to a lower energy state. Each element in the periodic table emits a characteristic set of discrete wavelengths when its atoms return from an excited state to a lower energy state. By detecting and analyzing these wavelengths, the elemental composition of a sample can be determined using a calibration curve showing the relationship between the spectral intensity ratio (absolute radiation power of an element/ absolute radiation power of the base metal) and the concentration of the element in the standard sample. The spectral light may be produced by irradiation with electromagnetic radiation such as by a laser or x-rays, but is generally produced by a short spark produced by a spark generator incident upon the target of which knowledge of the elemental composition is desired. Irrespective of the energy source, the accuracy and reliability of such emission spectrometers is dependent on the accuracy and quality of the detector and the optics used to receive the radiation emitted from the sample.

The output of a spectrometer may drift with time. Thus, drift correction may be required due to changes in the optics, the excitation source, processing electronics, and even ambient room temperature or humidity. These changes can cause drifts in the intensity ratios from those recorded during the initial calibration. In order to guarantee accuracy, detector and/or optics response should be checked and the spectrometer recalibrated, if necessary, using a reference material with a well-defined composition. The process of drift correction of the curves has many names: normalization, standardization, and re-calibration. Regardless of the name given the process, the curves are adjusted back to their state at the time of the original calibration.

If a drift correction is not made, errors will occur and false concentration readings will result. Timing for implementing drift correction is critical. However, this is determined by the individual laboratory based on the criticality of the analysis. Some laboratories periodically run check or SPC standards to determine if the instrument is within the allowed tolerances. The stability and duty cycle of the instrument determine the period for checking drift. It should at least be checked every hour or before a batch of samples are run to assure quality of results. If drift detection tolerances are not set up, it is imperative that drift correction, at a minimum, is accomplished every shift for laboratory instruments and hourly for mobile instruments. If the analyst is unsure about the state of the instrument, drift correction should immediately precede the analysis of any sample for optimum accuracy.

Since the spectral intensity ratio of a target sample to be analyzed is incorporated from a previously prepared and known reference calibration curve, the precision of the analysis for the target sample depends on the accuracy of the previously generated calibration curve. Accordingly, a standard reference material of homogeneous and known elemental content is necessary for accurate analysis. These standards should be selected to cover the concentration ranges of all elements for which the spectrometer is capable. The standards should also match the structure and alloy type being evaluated.

One such standard reference material used for the routine calibration is a circular ingot of, for example, 40 to 60 mm diameter. Prior to each use, the surface of the ingot must be prepared by grinding or milling in order to obtain a new active surface exhibiting no oxidation or other chemical changes in the surface. In this way, accurate measurement results can be obtained and a consistent calibration curve developed. The procedures and processes for obtaining representative analyses of metals are well known in the art. For example, Dulski, T. R. *A Manual for the Chemical Analysis of Metals*, ASTM International (1996) and the publication *ASTM E*1009 describe the analysis of carbon and low alloy steel. Reference materials are commercially available and known, for example, from the MBH catalogue 2014 from MBH Analytical LTD, Holland House, Queens Road, Barnet, ENS 4DJ, England.

According to published procedures such as USA standards ASTM E415-14 ("Standard Test Method for Analysis of Carbon and Low-Alloy Steel by Spark Atomic Emission Spectrometry") and ASTM E716-10 ("Standard Practices for Sampling and Sample Preparation of Aluminum and Aluminum Alloys for Determination of Chemical Composition by Spectrochemical Analysis"), Japan standards for steel JIS Z 2611 and JIS Z 2612 and for aluminum JIS H 1305, and European standards for steel DIN 51009 and for aluminum DIN 14726, grinding preparation of the sample is described, as well as that its surface should be free of contamination. Those in the analytical field are accustomed and trained to grind the standard reference material even when received in a protective shipping container. The referenced national standard procedures dictate that the renewal of the surface of the same sample provides a continuity of results. It is well known in the art that once the sample is prepared, the surface begins to deteriorate due to interaction with the environment.

As stated before, the accuracy of the analysis is dependent upon the quality of the recalibration, which in turn is dependent on the quality of the reference standard in terms of its composition and, more importantly, its preparation prior to analysis. The technique of sample preparation is known in the art. In some instances, it is a completely manual operation which is itself subject to minute variation. In a laboratory setting, this variation may be controlled to an acceptable level. In industrial environments where optical emission spectrographs are installed near a metallurgical process, these devices may be subject to the same rigorous process of recalibration. However, a higher frequency of recalibration may be necessary due to the environmental stress on the instruments. Routinely, one skilled in the recalibration process must travel to the location of the instrument or, in the case of mobile equipment, a field calibration or a return of the device to a certified calibration facility is necessary. Recalibration is a labor intensive and necessary endeavor costing a laboratory a considerable percentage of the analytical cost involved in the repeated preparation of the reference materials for calibration. The sample surface must be grounded or milled flat, free of residue from this process, and with a maximum tool impression on the surface. This preparation may be manual or automatic, but still requires the loading, retrieval, and segregation of the standard reference material.

Shipping reactive materials in inert gas, such as bottles or ampules, is common in the material supply industry. The use of protective coatings such as plastic covers, paints, oils, ceramic and CVD films are known in the art to prevent oxidation and corrosion protection of metal parts.

Metallic coatings are well known in the electrical contact industry for corrosion resistance. Silver coatings have been used to improve conductivity and provide corrosion resistance, as disclosed in U.S. Pat. No. 4,189,204 to Brown et al.

BRIEF SUMMARY OF THE INVENTION

It is an object of the present invention to provide a calibration method for a spectrometer and a reference material which facilitates the calibration of a spectrometer.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
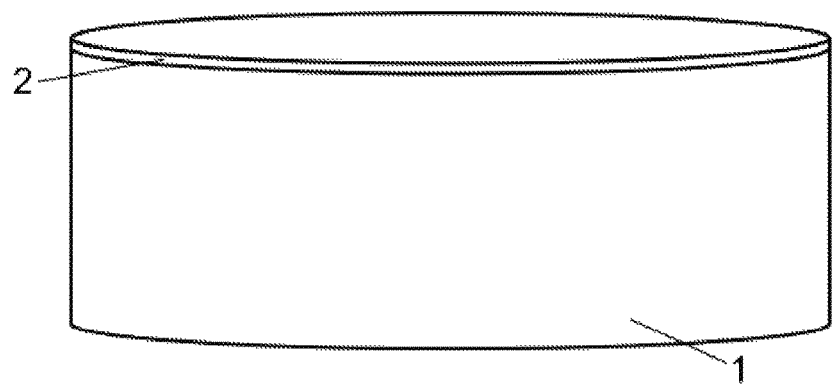
FIG. 1 is a three dimensional view of a reference material in the form of a coin according to an embodiment of the invention.

The object is therefore solved by a method for calibration of a spectrometer using a reference material which has a homogeneous content of elements. Further, the reference material is protected by an inert coating which protects a repeatable surface of the reference material. The reference material is used for calibration of the spectrometer in the "as received" condition, without additional preparation. "Inert" in the sense of the protective coating relates not to the absolute involatility of the element, but to the practical resistance to environment degradation, and more particularly to oxidation.

Due to the coating, it is not necessary to prepare a surface of the reference material by grinding or milling in order to obtain a new active surface exhibiting no oxidation or other chemical changes in the surface. Thus, the invention provides for a reduction in the technical effort.

Since an elaborate preparation is not required, automatic transfer of the reference material from a dispensing device to the spectrometer can take place for calibration, which allows for a further reduction in the required technical effort.

In a preferred embodiment of the invention, the reference material is kept under an inert gas atmosphere or vacuum within the dispensing device, which allows for long term storage of the reference material. Preferably, argon is used as the inert gas.

In a preferred embodiment of the invention, the composition of steel is measured by the spectrometer after the calibration. Steel is an alloy of iron and carbon. In a preferred embodiment of the invention, the compositions of all types of ferrous and nonferrous metals, including precious metals, alloys and ferroalloys, including as powdered metals, are measured by the spectrometer after calibration.

In a preferred embodiment of the invention, the inert coating does not comprise elements to be measured in the steel or iron alloy in order to avoid falsified results.

In a preferred embodiment, an inert gas is used to protect the homogeneous content instead of or in addition to the inert coating.

In a preferred embodiment of the invention, a plurality of reference materials, preferably in the form of coins, are inserted into a cassette comprising a lid prior to the calibration of a spectrometer.

In a preferred embodiment of the invention, one or more cassettes comprising a plurality of reference materials are inserted into a storage and dispensing device prior to the calibration of the spectrometer, in which the reference materials may be kept under vacuum or under an inert gas atmosphere from a remote supply. An inert gas (such as but not limited to argon) protects the recalibration surface and the protective coating of a reference material from environmental contamination.

In a preferred embodiment of the invention, a new reference material is removed periodically from such a cassette and transferred to a spectrometer platen for analysis or calibration. The entire operation can be performed without human intervention.

According to the invention, a reference material for calibration of a spectrometer has a homogeneous content of elements. The content is protected by an inert coating. In this way, there is an active surface which can be used for calibration of a spectrometer.

In a preferred embodiment of the invention, the inert coating is composed of a metal such as zinc, nickel, ruthenium, rhodium, palladium, silver, osmium, iridium, platinum, gold, or any alloys thereof.

In a preferred embodiment of the invention, the inert coating is composed of a noble metal such as Ag, Au, Pt, Ir and/or Rh or any alloy thereof. Noble metals are metals that are resistant to corrosion and oxidation on one side. As a rule, noble metals are not present in an iron alloy or in steel. For these reasons, a noble metal or any alloy thereof is an appropriate material.

It is preferred if the homogenous content of elements does not comprise an element of the inert coating. In a preferred embodiment of the invention, the homogeneous content is formed from steel.

In a preferred embodiment of the invention, the thickness of the inert coating is 0.1 to 10 µm, preferably 0.5 to 2 µm.

In a preferred embodiment of the invention, the reference material is a circular coin in order to facilitate handling, because alignment is not required when putting the circular coin into a housing or into a spectrometer platen for calibration.

In a preferred embodiment of the invention, the diameter of the coin is 10 to 80 mm diameter and/or the height of the coin is 1 to 30 mm.

In a preferred embodiment of the invention, the purity of the metal or the metal alloy is at least 90% and is preferably greater than 92.5%.

In another preferred embodiment, the reference material is arranged in a housing which is preferably closed gas-tightly. Thus, the invention is also directed to a housing containing at least one piece of the reference material. It is advantageous if more than one piece of the reference material is arranged in the housing. The pieces may be arranged such that they separated from each other. The housing may have at least two parts, whereby one part can be removed at least partially from the other part.

It is also preferred if the pieces are arranged in the housing one on top of the other.

The reference material is available for immediate use, without preparation, due to an anti-corrosive package, individually housed in an inert gas or vacuum-containing housing providing protection from environmental containments in the ambient environment such as atmosphere, particulate and contact contamination in handling, storage and use. The package or housing is sealed until use. Additionally, the portability of the reference material to remote sites allows calibration of mobile units and those installed near an industrial process.

The present invention provides an optical emission spectro-chemical reference material especially for metals and metal alloys having a homogeneous content of elements which is directly usable without preparation. Moreover, the present invention relates to a disposable spectro-chemical material that is available for immediate use, protected by an anti-corrosive coating, and is preferably housed in an inert gas-shielded container, providing protection from environmental containments in the ambient environment such as atmospheric, particulate and contact contaminants during handling, storage and use. It is capable for use in automatic recalibration routines of analytical equipment in remote locations as well as laboratory settings. Especially, the present invention is useful for a metallurgical process.

The application of an inert layer protects the recalibration surface during long term storage. This inert layer may also be combined with an inert atmosphere. A homogeneous coin of standard reference material according to the industrial standards known in the art is prepared with a surface finish according to a known industrial standard for analysis and calibration. A protective coating is immediately applied to its surface. The protective coating is selected in such a way that the coating material does not influence the analysis of the recalibration surface for elements that are of importance for the analysis. Examples (not limiting) of suitable materials in the case of reference materials used for steel are Ag, Au, Pt, Ir, Rh. The coating layer is, for example, applied using sputtering technology with high quality target material in order to obtain a pure layer (and is almost without the elements to be measured in steel/iron). An appropriate thickness of the layer is 1 µm, but other layer thickness may also be used.

In order to have sufficient corrosion resistance with silver (Ag) and further noble metals, a few µm is an appropriate layer thickness. Silver is characterized by poor sulfidation resistance and low hardness. However, silver has advantages over other non-oxidizing metals in that the element is not routinely analyzed as a contaminant in iron-based samples and its dominant spectral emission line does not interfere with others normally encountered in iron analysis. As a rule, this is also true for other noble metals.

The present invention provides the analytical laboratory with a reference standard which may be prepared in a predictable fashion with a predicable surface that is environmentally stable for extended periods of time. The elimination of the preparation labor, equipment, and consumable supplies provides considerable benefit to the cost of operation of an analytical instrument. The environmental stability of the reference standard provides a means for recalibration of an instrument installed at a metallurgical process location with the same precision as that of one installed in a controlled laboratory.

The use of an automatic standard reference loading apparatus for the recalibration of point-of-use spectrometers, i.e., shop floor installed analytical equipment, does not exist in the market. The potential benefit to the user's of point-of-use analysis equipment is optimized by an automatic recalibration system and no preparation samples are a key component to its realization.

Another distinct point of difference between this and all other standard reference materials known in the art is that the ready to use prepared surface of the present invention is two sided.

Referring to the figures, FIG. 1 is a view of a reference material in the form of a circular coin. The coin consists of known elemental content 1 and a coating 2 composed of silver or gold. The diameter of the coin is between 20 and 60 mm. The height of the coin is between 5 and 30 mm and the thickness of the coating 2 is between 0.5 and 5 µm.

The known elemental content 1 consists of steel, for example a low alloy steel comprising Fe, C, Si, S, P, Mn, Ni, Cr, Mo, Cu, Sn, Al, V, As, Zn, N, a ferritic and martensitic stainless steel comprising Fe, C, Si, S, P, Mn, Ni, Cr, Mo, Cu, Sn, V, Co, Nb, W, B, N, a high nitrogen stainless steel comprising Fe, C, Si, S, P, Mn, Ni, Cr, Mo, Cu, Al, V, W, Co, Nb, B, N. Further examples comprise Fe, C, Si, S, P, Mn, Ni, Cr, Mo, Cu, Sn, Al, As, Pb, N or Fe, C, Si, S, P, Mn, Ni, Cr, Cu, Al, Co, Mg, N.

Figure 2:
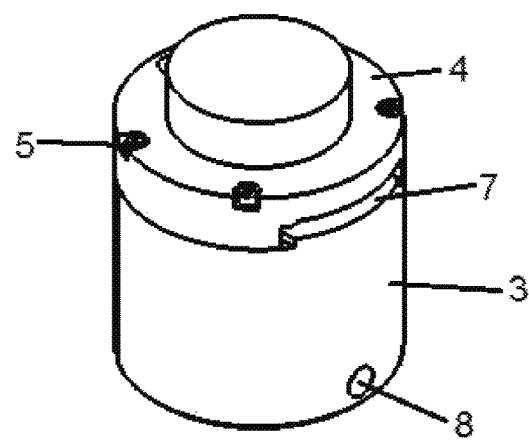
FIG. 2 is a three dimensional view of a cassette housing for the coins according to a further embodiment of the invention.
Figure 3:
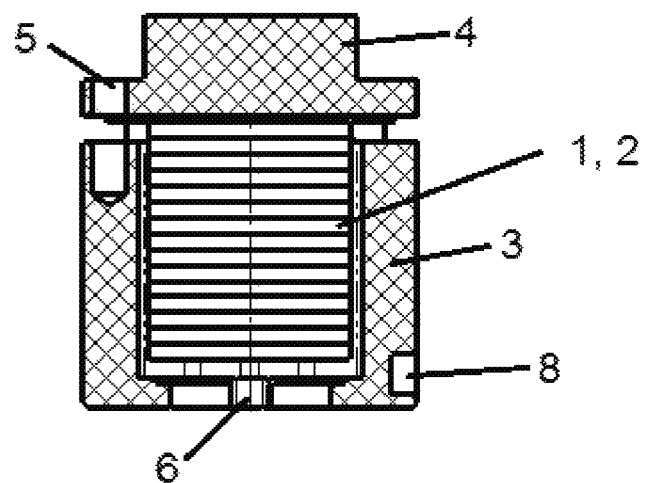
FIG. 3 is a sectional view of the cassette housing.

FIG. 2 is a three dimensional view of a cassette housing 3, 4 for the coins. FIG. 3 is a sectional view of the cassette housing 3, 4 comprising a plurality of coins 1, 2. It is possible to attach the lid 4 to the container 3 by one or more bolts 5.

Each coin 1, 2 is inserted into the cassette housing composed of a container 3 and a lid 4. The bottom of the container 3 comprises an inlet 6 for inert gas. There remains slit 7 between the container 3 and the lid 4 which allows removal of a coin 1, 2 from the cassette housing 3, 4 in an automatic manner. Further, the slit 7 may serve as an outlet for inert gas. The side wall of the container 3 may comprise a recess 8 which allows for fixing of the container 3 within a dispensing device.

Figure 4:
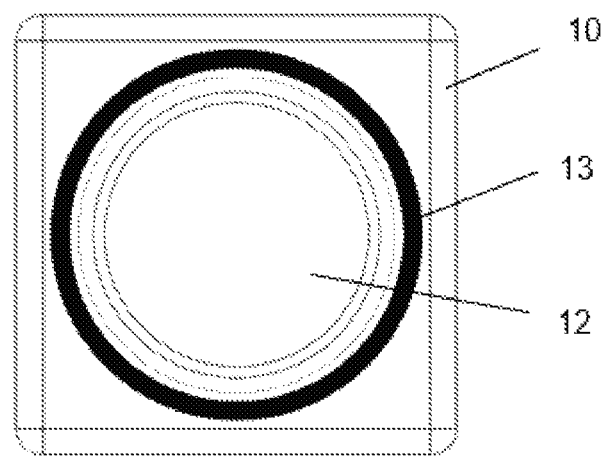
FIG. 4 is a housing for one piece of reference material.
Figure 5:
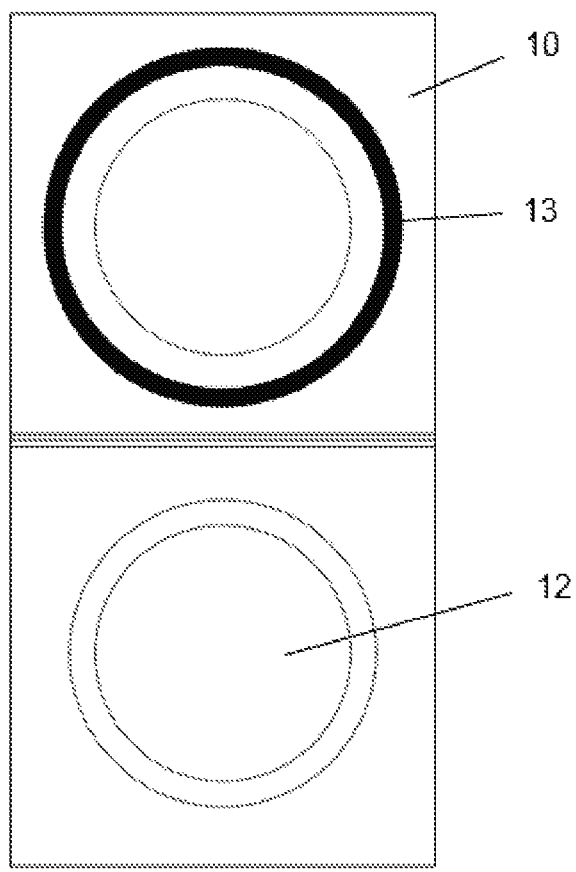
FIG. 5 shows the housing of FIG. 4, opened.
Figure 6:
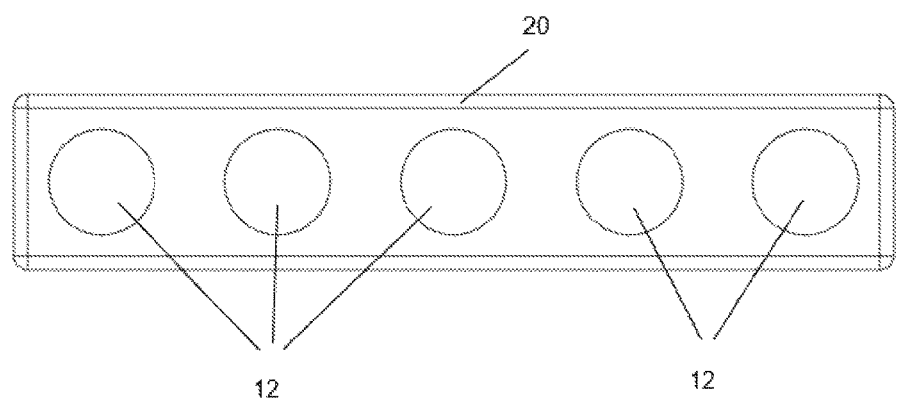
FIG. 6 shows a housing for multiple coins according to a further embodiment of the invention.
Figure 7:
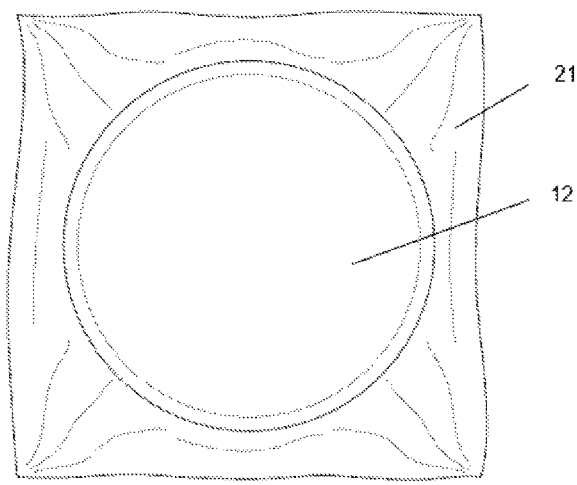
FIG. 7 is view of a housing according to a further embodiment of the invention.

In an alternative embodiment, each coin 12 of reference material is inserted into a housing 10, FIG. 4. The inert gas (for example argon, but others are possible) purges the internal space of the housing and is sealed by a gas tight closure of the housing, which protects the recalibration surfaces and its protective coating from environmental contamination. An O-ring 13, as one example, can be utilized for this purpose. The coin housing 10 is opened just prior to use, as shown in FIG. 5, and transferred to the spectrometer for analysis. Use of plastic bags, FIG. 6, is also contemplated. Multiple coins 12 can be housed in a foil backed holder 20, providing dispensing of individual coins 12 without compromising the inert gas protection for the remaining coins 12. This embodiment is similar to a blister pack used as a pill dispenser. Individual dispensing of coins 12 provides the operator with a recalibration surface without the need for preparation equipment. FIG. 7 is a familiar package 21 of multiple foils.

Figure 8:
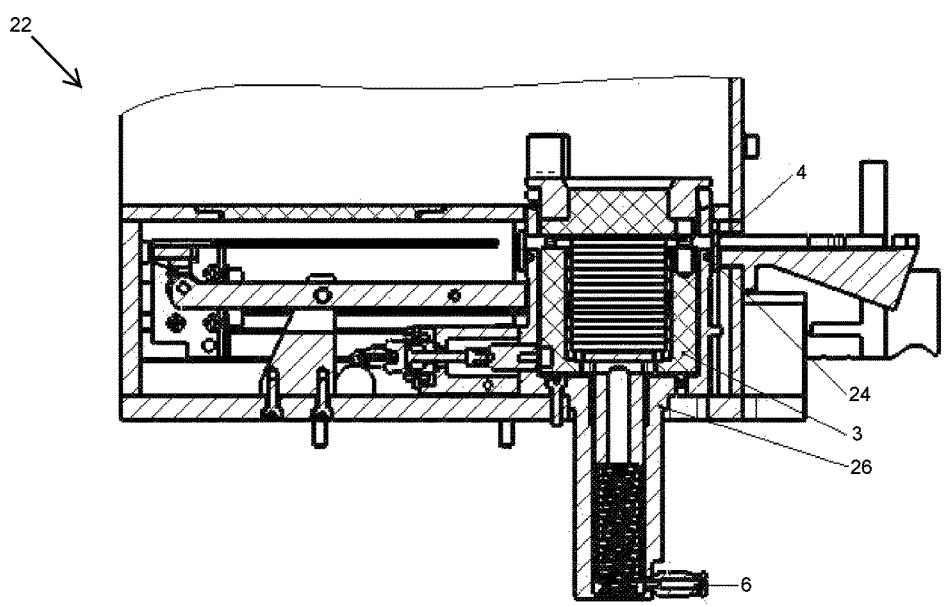
FIG. 8 is a view of a standard automatic loading apparatus according to a further embodiment of the invention.

An automatic standard reference loading apparatus 22 is shown in FIG. 8. Shown are the argon supply 6, cassette 3 with coins, cover ring 4, seal 24, and air-tight cassette with housing 26.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for calibrating an optical emission spectrometer comprising performing a calibration using a reference material, wherein the reference material is maintained under an inert atmosphere or vacuum prior to calibration, wherein the reference material comprises a homogeneous content of steel protected by an inert coating, and wherein the inert gas in combination with the inert coating protects the homogeneous content, wherein the steel is an alloy of iron and carbon, and wherein the spectrometer produces spectral light by a spark produced by a spark generator incident upon a target.

2. The method according to claim 1, further comprising automatically transferring the reference material from a dispensing device to the spectrometer prior to the calibration wherein an automatic standard reference loading apparatus is used for the automatic transfer.

3. The method according to claim 1, wherein the inert gas atmosphere is argon.

4. The method according to claim 1, further comprising measuring a composition of an iron alloy or a steel alloy with the spectrometer after the calibration.

5. The method according to claim 4, wherein the inert coating does not comprise components to be measured in the steel alloy or the iron alloy.

6. An optical emission spectrochemical reference material for calibration of an optical emission spectrometer, wherein the reference material is maintained under an inert atmosphere or vacuum prior to calibration, wherein the reference material comprises a homogeneous content of steel protected by an inert coating, and wherein the inert gas in combination with the inert coating protects the homogeneous content, wherein the steel is an alloy of iron and carbon, and wherein the spectrometer produces spectral light by a spark produced by a spark generator incident upon a target.

7. The reference material according to claim 6, wherein the inert coating comprises Ag, Au, Pt, Ir and/or Rh or alloys thereof.

8. The reference material according to claim 6, wherein the homogeneous content of steel does not comprise an element of the inert coating.

9. The reference material according to claim 6, wherein a thickness of the inert coating is 0.1 to 10 μm.

10. The reference material according to claim 6, wherein the reference material is a shape of a circular coin.

11. The reference material according to claim 10, wherein a diameter of the coin is 10 to 80 mm and/or a height of the coin is 1 to 30 mm.

12. The reference material according to claim 6, wherein the steel has a purity of at least 90%.

13. A housing comprising at least one piece of the reference material according to claim 6 arranged therein, wherein the housing is closed gas-tightly.

14. The housing according to claim 13, wherein the housing comprises more than one piece of the reference material arranged therein.

15. The housing according to claim 14, wherein the more than one piece of reference material are separated from each other.

16. The housing according to claim 13, wherein the housing comprises at least a first part and a second part, wherein the first part is removable at least partially from the second part.

17. The housing according to claim 14, wherein the more than one piece of reference material are arranged on top each other.

* * * * *